US012569197B2

(12) United States Patent
Scoggin, Jr.

(10) Patent No.: US 12,569,197 B2
(45) Date of Patent: Mar. 10, 2026

(54) METHODS AND APPARATUS FOR A BABY MONITORING GARMENT

(71) Applicant: SCOGGLEBERRIES DESIGN LLC, Appomattox, VA (US)

(72) Inventor: John Edward Scoggin, Jr., Appomattox, VA (US)

( * ) Notice: Subject to any disclaimer, the term of this patent is extended or adjusted under 35 U.S.C. 154(b) by 377 days.

(21) Appl. No.: 18/082,212

(22) Filed: Dec. 15, 2022

(65) Prior Publication Data

US 2023/0181110 A1 Jun. 15, 2023

Related U.S. Application Data

(60) Provisional application No. 63/289,760, filed on Dec. 15, 2021.

(51) Int. Cl.
| | |
|---|---|
| *A61B 5/00* | (2006.01) |
| *A61B 5/01* | (2006.01) |
| *A61B 5/1455* | (2006.01) |
| *A61B 5/28* | (2021.01) |
| *A61B 7/04* | (2006.01) |

(52) U.S. Cl.
CPC .............. *A61B 5/6804* (2013.01); *A61B 5/01* (2013.01); *A61B 5/14551* (2013.01); *A61B 5/28* (2021.01); *A61B 7/04* (2013.01); *A61B 2503/04* (2013.01); *A61B 2560/0214* (2013.01); *A61B 2562/166* (2013.01)

(58) Field of Classification Search
None
See application file for complete search history.

(56) References Cited

U.S. PATENT DOCUMENTS

| | | | |
|---|---|---|---|
| 6,687,523 | B1 | 2/2004 | Jayaramen et al. |
| 6,970,731 | B1 | 11/2005 | Jayaraman et al. |
| 7,559,902 | B2 * | 7/2009 | Ting ..................... A61B 5/6831 |
| | | | 600/300 |
| 7,650,176 | B2 | 1/2010 | Sarussi et al. |
| 8,094,013 | B1 | 1/2012 | Lee et al. |
| 9,126,122 | B2 | 9/2015 | Boeckle |
| 9,582,038 | B1 * | 2/2017 | Jayaraman ........... A61B 5/6804 |

(Continued)

FOREIGN PATENT DOCUMENTS

| | | |
|---|---|---|
| AU | 750158 B2 | 12/1999 |
| EP | 1198197 B1 | 4/2002 |

(Continued)

*Primary Examiner* — Carl H Layno
*Assistant Examiner* — Manolis Pahakis

(57) ABSTRACT

An infant monitoring device is described. The infant monitoring device may comprise a suit for an infant, at least one flexible printed circuit board (PCB) coupled with the suit, a main body receptacle coupled with the suit and operably coupled with the at least one flexible PCB, wherein the main body receptacle comprises at least one electrical contact operably coupled with the at least one flexible PCB and at least one temperature sensor operably coupled with the flexible PCB and operable to measure body temperature, and a main body device detachably coupled with the main body receptacle, the main body device comprising at least one contact point operable operably coupled with the at least one electrical contact of the main body receptacle and a battery operable to provide power to the main body device and the main body receptacle.

18 Claims, 16 Drawing Sheets

(56) References Cited

U.S. PATENT DOCUMENTS

| | | | |
|---|---|---|---|
| 9,693,730 B2 | 7/2017 | Workman et al. | |
| 9,933,298 B2 | 4/2018 | Likovich et al. | |
| 10,045,903 B2 | 8/2018 | Galitzer | |
| 10,123,739 B2 | 11/2018 | Cooper et al. | |
| 10,325,472 B1* | 6/2019 | Harsdorff | G08B 21/0446 |
| 10,499,837 B2 | 12/2019 | Workman et al. | |
| 10,918,222 B2 | 2/2021 | Galitzer | |
| 11,896,393 B1* | 2/2024 | McClung | A61B 5/303 |
| 2002/0097155 A1 | 7/2002 | Cassel et al. | |
| 2010/0201524 A1 | 8/2010 | Gallagher | |
| 2010/0274104 A1 | 10/2010 | Khan | |
| 2012/0136231 A1* | 5/2012 | Markel | A42B 1/006 |
| | | | 600/388 |
| 2013/0261415 A1 | 10/2013 | Ashe et al. | |
| 2013/0338472 A1* | 12/2013 | Macia | A61B 5/02055 |
| | | | 174/255 |
| 2015/0148619 A1* | 5/2015 | Berg | A61B 5/6804 |
| | | | 600/300 |
| 2016/0278658 A1* | 9/2016 | Bardy | A61B 5/6833 |
| 2016/0287097 A1* | 10/2016 | Pradeep | G16H 40/63 |
| 2017/0258402 A1* | 9/2017 | Acquista | A61B 5/305 |
| 2018/0093121 A1* | 4/2018 | Matsuura | G09B 19/0038 |
| 2018/0249944 A1* | 9/2018 | Poutiatine | G01J 1/429 |
| 2018/0263521 A1* | 9/2018 | Stordopoulos | A61B 5/316 |
| 2019/0201772 A1* | 7/2019 | Beamer | A61B 5/08 |
| 2019/0209028 A1* | 7/2019 | Baxi | A61B 5/28 |
| 2019/0261874 A1* | 8/2019 | Berg | A61B 5/0205 |
| 2021/0100460 A1* | 4/2021 | Dagdeviren | G01K 13/20 |
| 2021/0196975 A1* | 7/2021 | De Taboada | A61B 5/6804 |
| 2021/0244941 A1* | 8/2021 | Daniels | A61N 1/36003 |
| 2022/0015648 A1* | 1/2022 | Zinner | H04R 1/028 |
| 2023/0014669 A1* | 1/2023 | Lynch | A61B 5/6804 |
| 2024/0008815 A1* | 1/2024 | Riaz | D06N 3/0077 |

FOREIGN PATENT DOCUMENTS

| | | | | |
|---|---|---|---|---|
| WO | 2001001855 A1 | 1/2001 | | |
| WO | 2004075750 A1 | 9/2004 | | |
| WO | WO-2020099503 A1 * | 5/2020 | | G08B 21/0211 |

* cited by examiner

Right arm ECG transfer in snap button

METHODS AND APPARATUS FOR A BABY MONITORING GARMENT

CROSS REFERENCE TO RELATED APPLICATIONS

This application claims the benefit of U.S. Provisional Patent Application No. 63/289,760, filed Dec. 15, 2021.

BACKGROUND

Despite progress in infant monitoring technology, there are still thousands of infants that die each year. Parents and caretakers of infant children also want to be able to monitor the children in their care more closely. Despite various developments in infant monitoring, infants continue to die from preventable causes.

SUMMARY

Embodiments of the invention include a system for monitoring an infant's health. Embodiments include an infant monitoring device, that may comprise a suit for an infant, at least one flexible printed circuit board (PCB) coupled with the suit, a main body receptacle that may be coupled with the suit and operably coupled with the at least one flexible PCB, wherein the main body receptacle may comprise at least one electrical contact that may be operably coupled with the at least one flexible PCB and at least one temperature sensor that may be operably coupled with the flexible PCB and may be operable to measure body temperature and a main body device detachably coupled with the main body receptacle, wherein the main body device may comprise at least one contact point that may be operable to be operably coupled with the at least one electrical contact of the main body receptacle and a battery that may be operable to provide power to the main body device and the main body receptacle.

Embodiments may include the infant monitoring device described above, wherein the main body receptacle may further comprise at least one electrocardiogram sensor operably coupled with the at least one flexible PCB.

Embodiments may include the infant monitoring device described, wherein the main body receptacle may further comprise at least one pulse oximeter sensor operably coupled with the at least one flexible PCB.

Embodiments may include the infant monitoring device described, wherein the main body receptacle may further comprise at least at least one electronic stethoscope operably coupled with the at least one flexible PCB.

Embodiments may include the infant monitoring device described, wherein the main body device may further comprise at least one external charging connection, an LCD screen, and a UV sensor.

Embodiments may include the infant monitoring device described, that may further comprise a plurality of sensors and wherein the at least one electrical contact may comprise a plurality of electrical contacts; and the at least one flexible PCB may comprise a plurality of flexible PCBs, wherein the plurality of electrical contacts may be operably coupled with the plurality of flexible PCBs; and, wherein each of the plurality of sensors may be operably coupled with to each of the plurality of flexible PCBs.

Embodiments may include the infant monitoring device described, wherein each of the plurality of sensors may be operably connected to each of the plurality of flexible PCBs via wired connections.

Embodiments may include the infant monitoring device described, wherein the plurality of sensors may comprise at least one of at least one extremity temperature sensor, at least one electrocardiogram sensor, and at least one extremity pulse oximeter sensor.

Embodiments may include the infant monitoring device described, wherein wires of the wired connections may be routed along seams of the suit.

Embodiments may include the infant monitoring device described, wherein the suit may comprise a plurality of snap buttons, wherein at least one of the plurality of snap buttons may be electrically conductive.

Embodiments may include the infant monitoring device described, wherein the at least one of a plurality of electrically conductive snap buttons may be a transfer switch.

Embodiments may include the infant monitoring device described, wherein the at least one of a plurality of electrically conductive snap buttons may comprise a 3-volt line transfer.

Embodiments may include the infant monitoring device described, wherein the at least one of a plurality of electrically conductive snap buttons may comprise a transfer switch operably coupled to the at least one electrocardiogram sensor.

Embodiments may include the infant monitoring device described, wherein the suit may comprise a conductive fabric operably coupled to the connection device, wherein the conductive fabric may be operable to provide the at least one electrocardiogram sensor with electrical impulses from a wearer's body.

Embodiments may include the infant monitoring device described, that may further comprise a video-capture device external to the suit, wherein the video-capture device may comprise a power charging station operable to couple with the main body device at the at least one external charging connection.

Embodiments may include the an infant monitoring device, that may comprise a suit for an infant; at least one flexible printed circuit board (PCB) that may be coupled with the suit; a main body receptacle coupled with the suit and may be operably coupled with the at least one flexible PCB, wherein the main body receptacle may comprise at least one electrical contact that may be operably coupled with the at least one flexible PCB and at least one temperature sensor that may be operably coupled with the flexible PCB and may be operable to measure body temperature; a gyroscope that may be operably coupled to the at least one electrical contact; at least one electrocardiogram sensor that may be coupled to the main body receptacle and may be operably coupled to the at least one electrical contact; at least one pulse oximeter sensor that may be coupled to the main body receptacle and may be operably coupled to the at least one electrical contact; and at least one electronic stethoscope that may be coupled to the main body receptacle and may be operably coupled to the at least one electrical contact; and a main body device that may be detachably coupled with the main body receptacle, the main body device may comprise at least one contact point that may be operable to be operably coupled with the at least one electrical contact of the main body receptacle; a battery charging port; a rechargeable battery that may be operable to provide power to the main body device and the main body receptacle; a processor that may be operably coupled with the at least one electrical contact; a memory that may be in communication with the processor; a transceiver in that may be communication with the processor and the memory, wherein the transceiver may be operable to transmit information to an external location and receive information from an external location; a screen that may be operably coupled with the processor and the memory, wherein the screen may be operable to display information related to measurements taken by the infant monitoring device; and an ultraviolate light sensor that may be coupled with the display.

Embodiments may include the infant monitoring device described, that may further comprise at least one extremity temperature sensor that may be operably coupled with the at least one electrical contact.

Embodiments may include the infant monitoring device described, that may further comprise at least one extremity echocardiogram sensor that may be operably coupled with the at least one electrical contact.

Embodiments may include an infant monitoring device, that may comprise a resting mat; at least one flexible printed circuit board (PCB) that may be coupled with the mat; a main body receptacle that may be coupled with the mat and that may be operably coupled with the at least one flexible PCB, wherein the main body receptacle may comprise at least one electrical contact that may be operably coupled with the at least one flexible PCB; a main body device that may be detachably coupled with the main body receptacle, wherein the main body device may comprise at least one contact point that may be operable to be operably coupled with the at least one electrical contact of the main body receptacle and a battery that may be operable to provide power to the main body device and the main body receptacle; at least one pressure point on the resting mat, the at least one pressure point may detect movement, wherein one the mat, the at least one pressure point being may be operably coupled with the at least one electrical contact.

Embodiments may include the infant monitoring device described, that may further comprise a Bluetooth or near field communication device that may be operably coupled with the main body device and may be operable to communicate data from the main body device to an external location.

The various embodiments described in the summary and this document are provided not to limit or define the disclosure or the scope of the claims.

DETAILED DESCRIPTION

Figure 1:
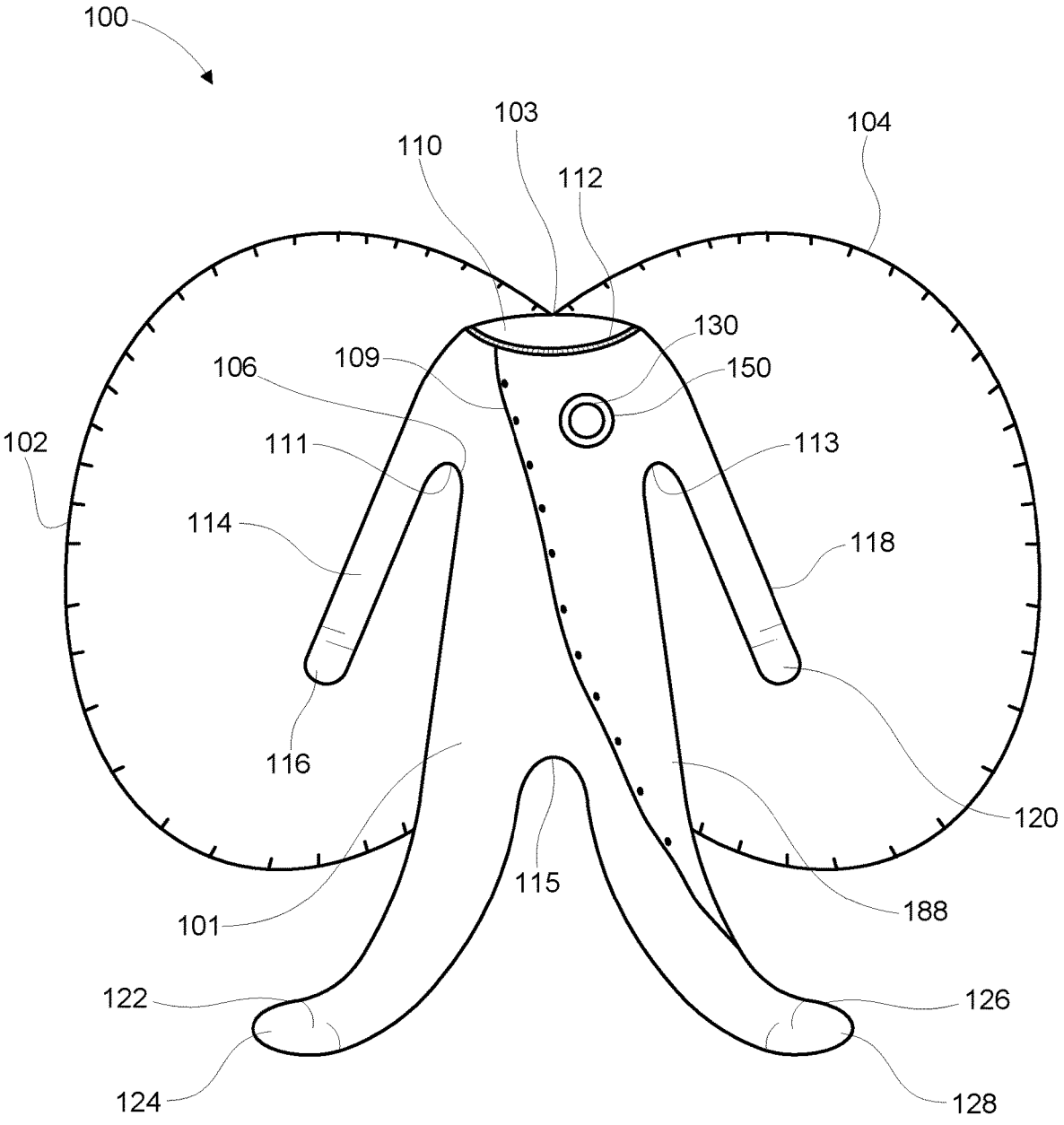
FIG. 1 is an illustration of a front view of an infant monitoring garment and system.

Some embodiments include an infant swaddle suit 100 as shown in FIG. 1. The infant swaddle suit 100 may comprise a swaddle body 101. The infant swaddle suit 100 may comprise a first swaddle ear 102 coupled to a back side of the swaddle suit 100. The infant swaddle suit 100 may comprise a second swaddle ear 104 coupled to a back side of the swaddle suit 100. The second swaddle ear 104 may be coupled to the back side of the swaddle suit 100 adjacent to first swaddle ear 102. The first swaddle ear 102 and the second swaddle ear 104 may wrap around the swaddle body 101 and other elements of the swaddle suit 100, which will be described herein below.

The swaddle suit body 101 may comprise a first front member 104 and a second front member 106. The first front member 104 and the second front member 106 may be detachably coupled together by at least one snap 145 as will be discussed herein below.

The swaddle suit body 101 may comprise a neck opening 110. The neck opening 110 may be formed when the first front member 106 and the second front member 108 are joined together.

The swaddle suit 100 may comprise a first arm 114 coupled with the first front member 104 and the back 103. The first arm 114 may comprise a first wrist opening 116. The swaddle suit 100 may comprise a second arm 118 coupled with the second front member 106 and the back 103. The second arm 116 may comprise a second wrist opening 120.

The swaddle suit 100 may comprise a first leg 122 coupled with the first front member 104 and the back 103. The first leg 122 may comprise a first foot 124. The swaddle suit 100 may comprise a second leg 126 coupled with the first front member 104, the second front member 106, and the back 103, as shown in FIG. 1. The second leg 126 may comprise a second foot 128.

The second front member 108 may comprise an opening 150. The opening 150 may comprise at least one flexible printed circuit board (PCB) 154, as will be discussed below in connection with at least FIG. 2A. A main body receptacle 134 may be operable to fit within or over the opening 150. A main body device 130 may be operable to fit about the opening 150 and may be operable to couple with a main body receptacle 134, as discussed herein below.

Figure 2A:
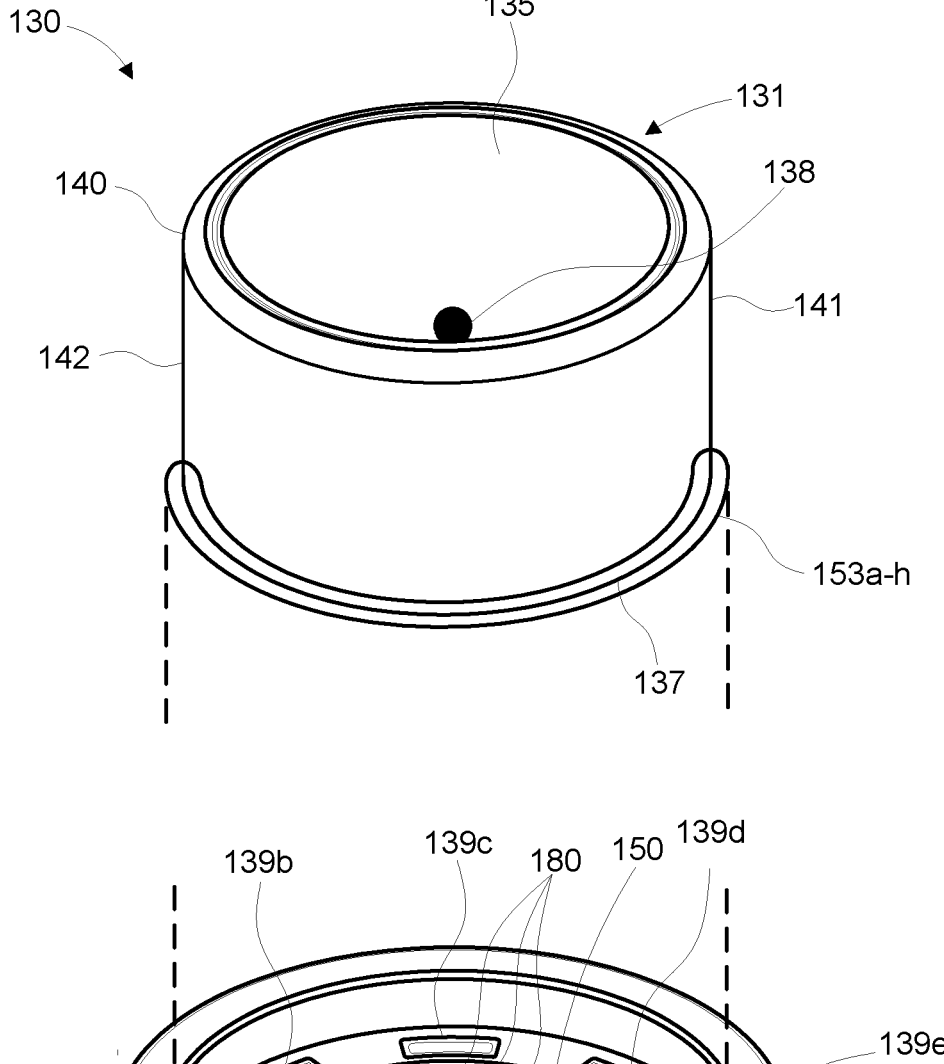
FIG. 2A is an illustration of a feature of the infant monitoring system.
Figure 2B:
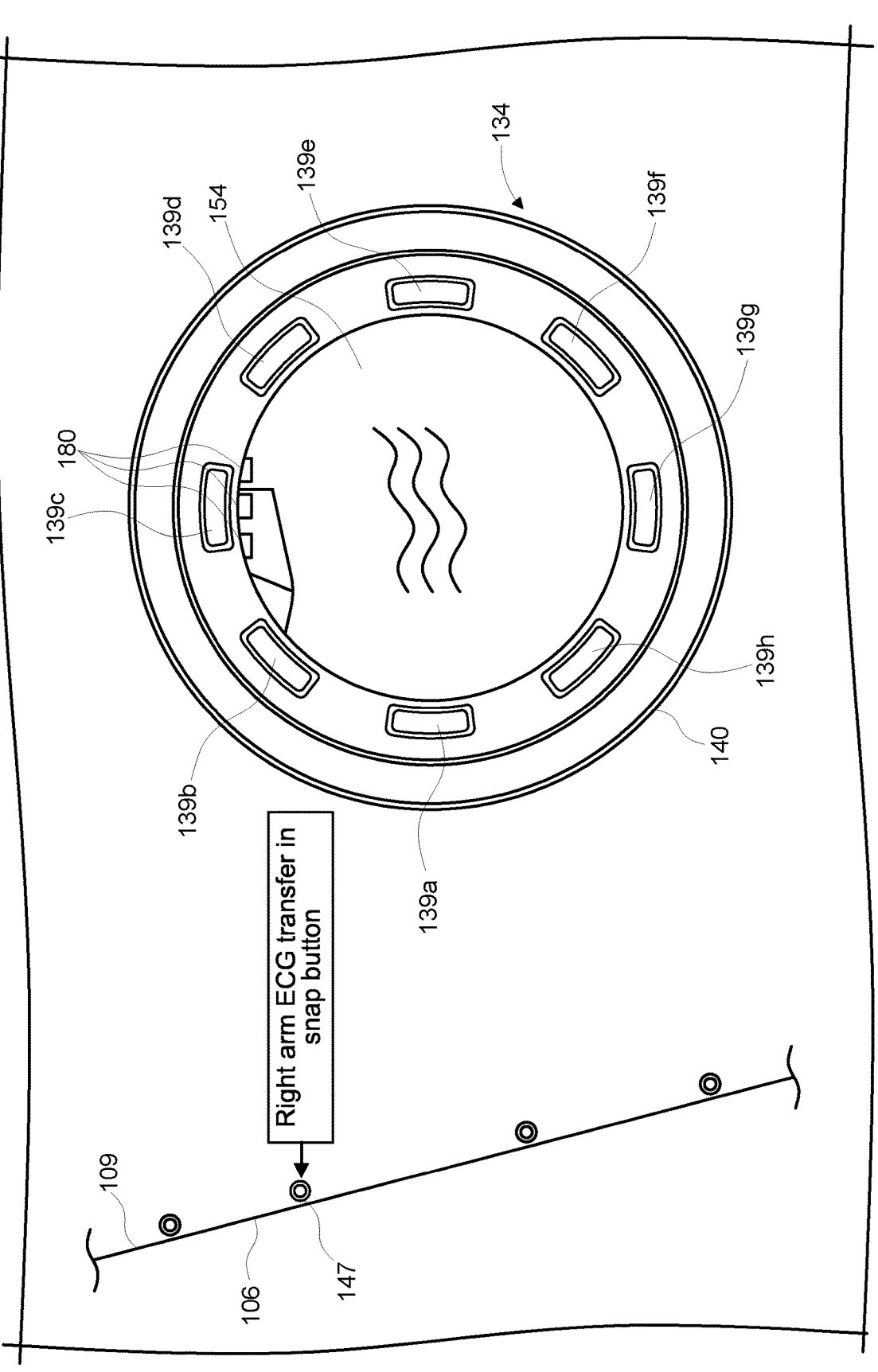
FIG. 2B is an illustration of a feature of the infant monitoring system.
Figure 2C:
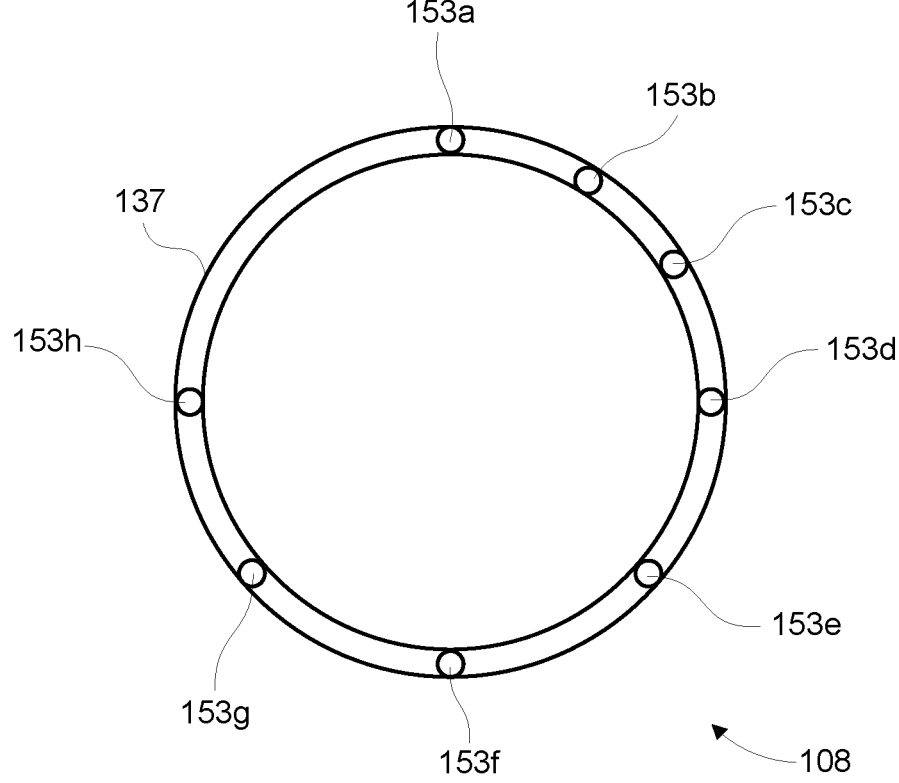
FIG. 2C is an illustration of a feature of the infant monitoring system.

The main body device 130 and related components are shown in further detail in FIGS. 2A-2C.

FIG. 2A shows an illustration of the main body receptacle 134 mounted on or within the opening 150. In some embodiments, the opening 150 may be filled with flexible PCB 154. The flexible PCB 154 may serve as a diaphragm for the various components of the swaddle suit 100, as described herein. The flexible PCB 154 may be the electrical connection for various components and sensors described herein below. The flexible PCB 154 is represented by the lines 154;

however, it should be noted that in some embodiments, the flexible PCB 154 may fill the entire space of the opening 154.

As shown in FIG. 2A, in some embodiments, the main body receptacle 134 may comprise various components. The main body receptacle 134 may comprise a housing 143. In some embodiments, the housing 143 may be coupled with the opening 150. In some embodiments, the housing 143 may be operably electronically coupled with the flexible PCB 154 to provide contact between various components of the swaddle suit 100 as will be described herein. In some embodiments, the housing 143 may be detachably coupled with or within the opening 150. In some embodiments, the housing 143 may be permanently coupled with or within the opening 150. In some embodiments, the housing 143 may be detachably coupled with the flexible PCB 154. In some embodiments, the housing 143 may be permanently coupled with the flexible PCB 154.

In some embodiments, the flexible PCB 154 may be integrated into the fabric of the second member 108 of the swaddle suit 100.

As shown in FIG. 2A, the housing 143 may support various components coupled to the housing 143. In some embodiments, the housing 143 may comprise at least one contact 139. As shown in FIG. 2A, the housing 143 may comprise multiple contact points 139a, 139b, 139c, 139d, 139e, 139f, 139g, and 139h. In some embodiments there may be more contact points. In some embodiments, there may be fewer contact points. Each contact point 139a-139h may correspond to a different sensor within the swaddle suit 100. Each contact 139a-139h may transfer a unique wire signal received from the flexible PCB 154.

For example, in some embodiments, contact point 139a may correspond to a temperature sensor for a wearer's extremities. In some embodiments, contact point 139b may correspond to pulse oximeter associated with a wearer's left arm or hand. In some embodiments, contact point 139c may correspond to pulse oximeter associated with a wearer's left leg or foot. In some embodiments, contact point 139d may correspond to a ground wire. In some embodiments, contact point 139e may correspond to an ECG sensor associated with a wearer's left arm or hand. In some embodiments, contact point 139f may correspond to a wearer's legs. In some embodiments, contact point 139g may correspond to an ECG sensor associated with a wearer's right arm or hand. In some embodiments, contact pad 139h may correspond to a 3 volt contact pad.

In some embodiments, the housing 143 may comprise a pulse oximeter 180 as described below. The pulse oximeter 180 may monitor heart rate and blood-oxygen saturation. In some embodiments, the pulse oximeter 180 may be electrically coupled or mounted to the flexible PCB 154 and may be hidden within the housing 143 of the main body receptacle 134.

In some embodiments, the pulse oximeter 180 may take and/or receive the measurements from the contact the pulse oximeter 180 may have with the skin of a wearer. In some embodiments, the pulse oximeter 180 may be in contact with a wearer's chest beneath the opening 150 and/or the main body receptacle 143.

Referring still to FIG. 2A, the swaddle suit 100 may further comprise a main body device 130. The main body device may comprise a housing 131. The housing 131 may be operable to support various components coupled with the housing 131.

In some embodiments, the main body device 130 may be detachably coupled with the main body receptacle 134, as shown by the dashed lines in FIG. 2A.

In some embodiments, the housing 131 may comprise a contact housing 137. The contact housing 137 may comprise at least one electrical contact 153 point operable to be electrically coupled with a contract 139 within the main body receptacle 143. Referring to FIG. 2C, a representation of contact housing 137 is illustrated, showing a representation of various electrical contacts. In some embodiments, the electrical contact point 153 may comprise multiple contact points 153a, 153b, 153c, 153d, 153e, 153f, 153g, and 153h. For example, in some embodiments, contact point 153a may correspond to a temperature sensor for a wearer's extremities. In some embodiments, contact point 153b may correspond to pulse oximeter associated with a wearer's left arm or hand. In some embodiments, contact point 153c may correspond to pulse oximeter associated with a wearer's left leg or foot. In some embodiments, contact point 153d may correspond to a ground wire. In some embodiments, contact point 153e may correspond to an ECG sensor associated with a wearer's left arm or hand. In some embodiments, contact point 153f may correspond to a wearer's legs. In some embodiments, contact point 153g may correspond to an ECG sensor associated with a wearer's right arm or hand. In some embodiments, contact pad 153h may correspond to a 3 volt contact pad.

In some embodiments, the main body device 130 may comprise a charging port and may be operable to connect to a charging station and operably couple the charging station. The main body device 130 may comprise a battery and may be charged and recharged for repeated uses.

Referring again to FIG. 2B, the body 131 may comprise an LCD screen 135. The LCD screen 135 may be coupled with a processor and may display information gathered by various sensors as described below. The body 131 may comprise a UV sensor 138.

The body 131 may comprise various components that may receive and process data from the swaddle suit 100 and that may transmit data to an external server or to a smart device. The body 140 may comprise an electrocardiogram 170, as described below. The electrocardiogram 170 may be configured to monitor an infant's heart rate via electrical impulses produced by the body.

The body 140 may comprise a temperature sensing system coupled with a series of temperature sensors, as described below. The body 140 may also comprise a core temperature sensor 136 that may measure the core temperature of an infant. The core temperature sensor 136 may be electronically coupled with the flexible PCB 154. In some embodiments, the main body device may be in communication with a home heating and air conditioning system. Should the infant's temperature be out of a normal or comfortable range, the home heating and air conditioning system may be activated to warm or cool the environment as needed.

In some embodiments, the swaddle suit 100 may further comprise an electronic stethoscope 141. In some embodiments, the electronic stethoscope may be comprised of multiple parts, which are coupled together when the main body device 130 is coupled with the main body receptacle 134. The electronic stethoscope may comprise a sensor within the body 143. The electronic stethoscope 141 may receive an acoustic signal representing an infant's heartbeat. The processor within the main body device 130 may use extrapolate heart rate and breathing aspirations using digital signal processing and artificial intelligence to monitor heart rate and perform an early diagnosis of respiratory and heart disease. All hardware infrastructure needed to receive and process the sensor signals may be contained with the body 140.

The body 140 may comprise a gyroscope 142. The gyroscope 142 may monitor aspirations by measuring the rise and fall of an infant's chest. The gyroscope 142 may be electronically coupled with and in communication with the flexible PCB 154. The gyroscope 142 may communicate its measurements and readings to the flexible PCB 154. Similar to the other measurements and readings disclosed herein, the flexible PCB 154 may pass those readings and measurements to the main body device 130 for processing and transmission to an outside location.

In some embodiments, the main body device 130 may process the readings and measurements from the stethoscope 141 and the gyroscope 142. Routine motions, such as infant feedings and diaper changes, may be detected, identified, and tracked. Tracking such events may assist health care professionals to identify multiple conditions such as malnutrition, hydration or dehydration, bowel blockages and other conditions that may lead to more serious health situations, such as bowel jaundice and sepsis. Tracking such routine events in infancy may assist parents who may be experiencing many challenges that come with being a parent to a newborn baby, such as sleep deprivation. In some embodiments, the main body device 130, or associated external computing devices may, through machine learning and predictive algorithms, provide suggestions to a parent or caretaker regarding feeding or a diaper change, or other care, as may be required or advisable.

In some embodiments, the main body device 130 and main body receptacle 134 may operate as a standalone unit strapped around an infant's chest and may communicate readings and measurements related to core temperature, breathing, heart activity, and other vital measurements as described herein to an external location.

Figure 3:
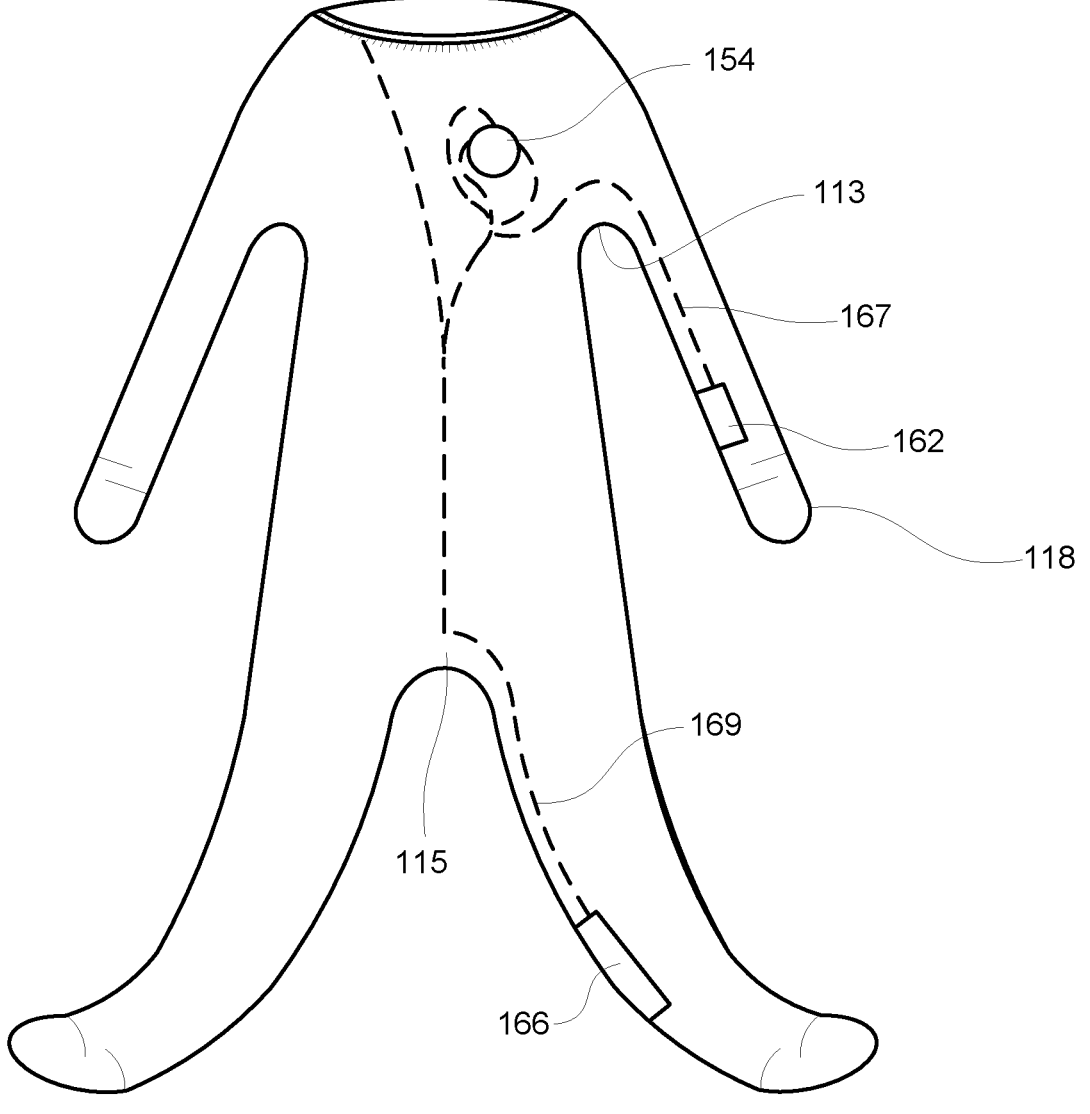
FIG. 3 is an illustration of a front view of the infant monitoring garment showing various internal components.

Referring now to FIG. 3, in some embodiments, the swaddle suit 100 may comprise a temperature sensor 162 located on the left arm 118 proximate to the wrist 120. The temperature sensor 162 may be operably coupled with the flexible PBC 154 via wire 167. The wire 167 may comprise a package of three wires. The three wires may comprise a three-volt (3V) wire, a data wire, and a ground wire. The wire 167 may be coupled with the flexible PBC 154, and subsequently, the main body device 130 via at least one transfer point in a snap button, as detailed above with respect to the first temperature sensor 161.

In some embodiments, the wire 167 may be placed in the swaddle suit 100 along the sewed seam for as far as possible, until approximately the armpit 113, at which point the 3V wire, data wire, and ground wire split to travel to their respective locations in the flexible PCB 154.

In some embodiments, the swaddle suit may comprise a second temperature sensor 166 located on the left leg 126 proximate to the foot 128. The second temperature sensor 166 may be operably coupled with the contact pad 14 via wire 169. The wire 169 may comprise a package of three wires. The three wires may comprise a three-volt (3V) wire, a data wire, and a ground wire. The wire 169 may be coupled with the flexible PBC 154.

In some embodiments, the wire 169 may be placed in the swaddle suit 100 along the sewed seam for as far as possible, until approximately the groin 115. The wire 169 may continue as a package until reaching an area proximate the flexible PCB 154, at which point 3V wire, data wire, and ground wire split to travel to their respective locations of the flexible PCB 154.

Each of the temperature sensors described herein may be housed within a conductive fabric.

Figure 4:
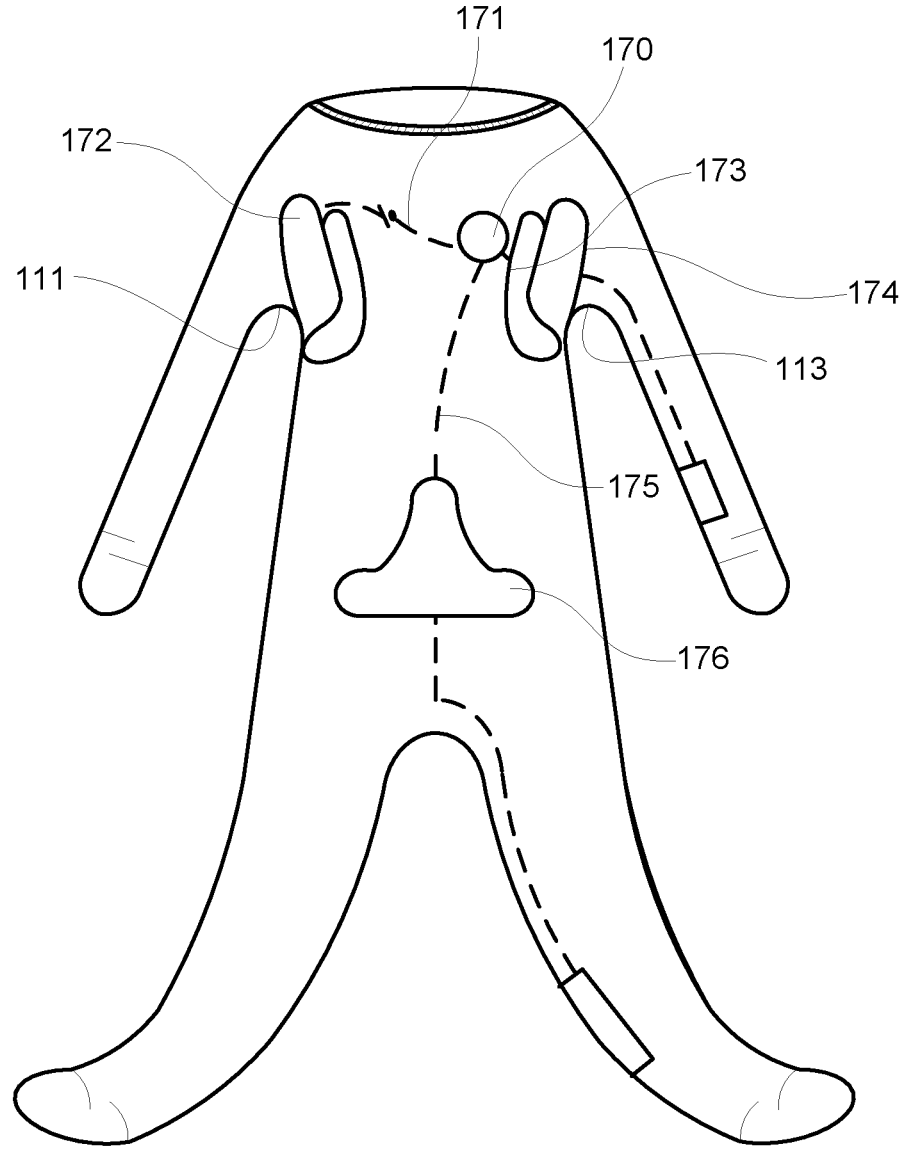
FIG. 4 is an illustration of a front view of the infant monitoring garment showing various internal components.

Referring now to FIG. 4, in some embodiments the swaddle suit 100 may comprise an electrocardiogram 170. The electrocardiogram may be comprised within the main body device 130. The electrocardiogram 170 may record naturally occurring electrical impulses within the body that coordinate contractions of the different parts of the heart to maintain blood flow. The electrocardiogram 170 may be operably coupled with at least one sensor pad 172 via lead wire 171. The at least one sensor pad 172 may be positioned approximately at the armpit 111 on the inside of the swaddle suit 100. When the swaddle suite 100 is being worn by an infant, the at least one sensor pad 172 may be in contact with the skin of the infant near to the armpit 111. The at least one sensor pad 172 may receive and communicate to the electrocardiogram 170 heart activity in the form of electrical impulses.

The at least one sensor pad 172 may comprise a sensor pad 174. The sensor pad 174 may be positioned approximately at the armpit 113 on the inside of swaddle suit 100. The at least one sensor pad 172 may receive and communicate to the electrocardiogram 170, via lead wire 173, heart activity in the form of electrical impulses.

The at least one sensor pad 172 may comprise a sensor pad 176. The sensor pad 176 may be positioned approximately at the front section of the swaddle suit 100, at approximately the abdominal region, on the inside of swaddle suit 100. In some embodiments, the sensor pad 176 may be located along a rear portion of a suit, along a spinal area of the abdominal region. The at least one sensor pad 176 may receive and communicate to the electrocardiogram 170, via lead wire 175 heart activity in the form of electrical impulses.

In some embodiments, the at least one sensor pad 172 may comprise additional sensors. In some embodiments, each sensor pad 172, 174, 176 may be in contact with a conductive fabric. The conductive fabric may facilitate the sensor pads 172, 174, and 176 receiving the body's electrical impulses.

Figure 5:
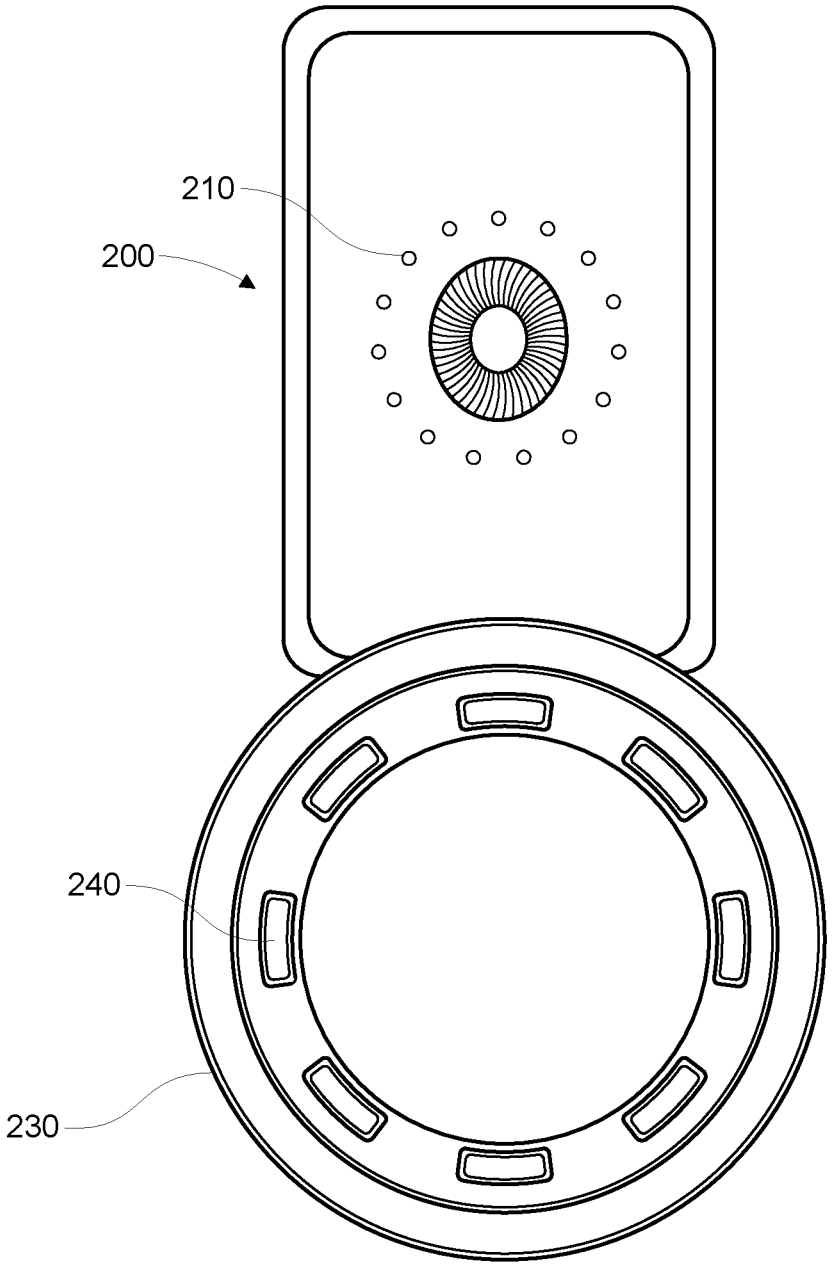
FIG. 5 is an illustration of a feature of the infant monitoring system.

Referring now to FIG. 5, some embodiments may include a video capture device 200. The video capture device 200 may comprise various components to capture and process video and audio. The video capture device 200 may comprise various components to and transmit video and audio signals to an external server and/or interface. For example, the video capture device 200 may comprise an optical capture device. The video capture device 200 may comprise at least one infrared light 210. The infrared light 210 may be activated in a dark environment and may facilitate capturing optical images in the absence of light. In some embodiments, the video capture device 200 may comprise a microphone.

In some embodiments, the video capture device 200 may comprise a processor capable of processing video signals. In some embodiments, the processor may be capable of processing audio signals. In some embodiments, the video capture device 200 may comprise a transceiver. The transceiver may be operable to send video and/or audio signals to a server or to a connected device, such as smart electronic device, such as a smart phone, a smart tablet, a computer, or a smart tv. In some embodiments, the transceiver may be operable to receive communications from a server. In some embodiments, the video capture device 200 may be coupled to a power supply.

In some embodiments, the video capture device 200 may be coupled with a charging station 230, as shown in FIG. 5. The charging station 230 may be coupled to a power supply. The charging station 230 and may share the power supply of the video capture device 200. The charging station 230 may comprise at least one charging contact point 240. The at least one charging point 240 may be operable to couple with the external contacts 137 of the main body device 130 and electrically charge the main body device 230.

Figure 6:
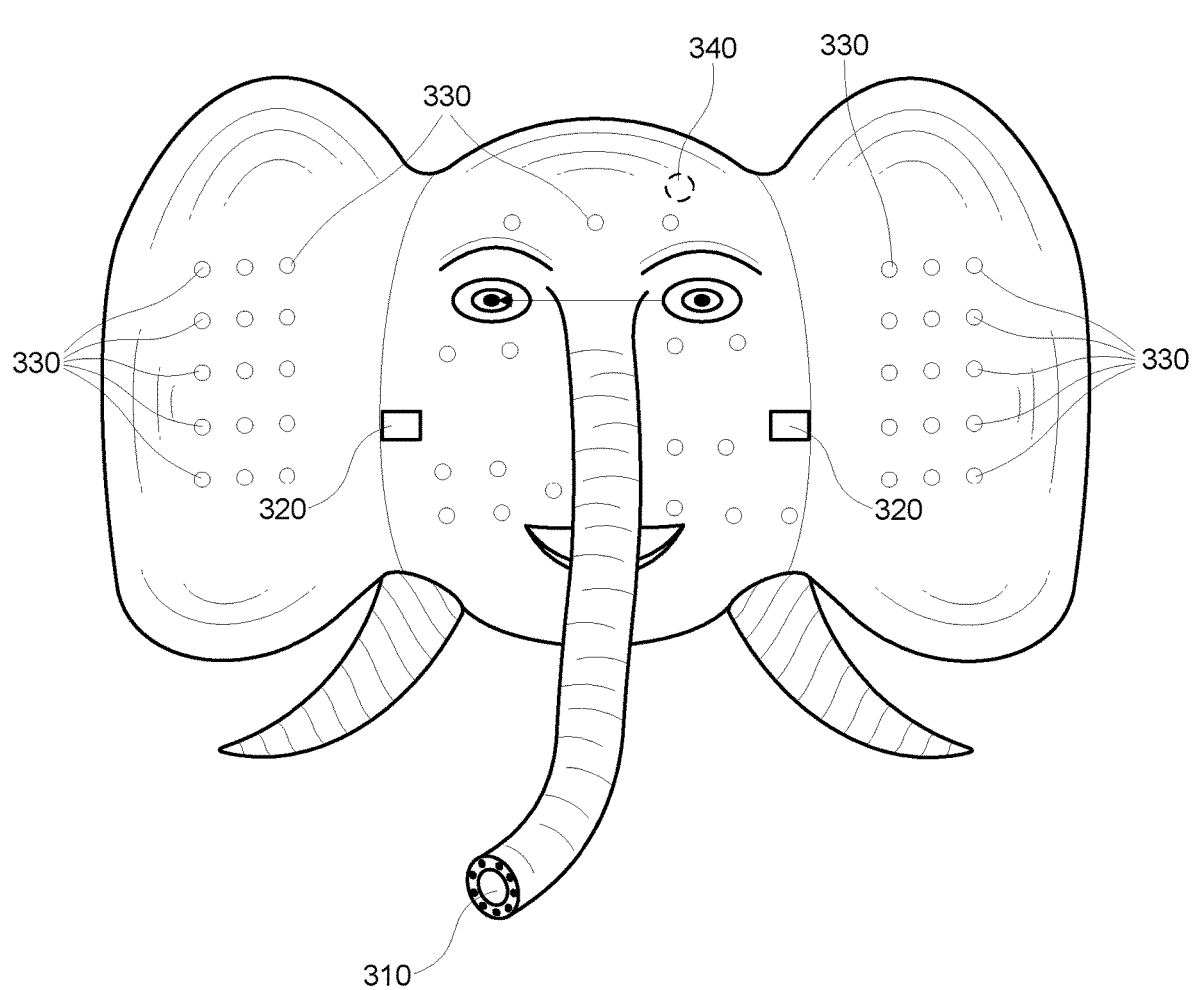
FIG. 6 is an illustration of a feature of the infant monitoring system.

In some embodiments, the main body device 130 may be operable to couple with a resting mat 300, as shown in FIG. 6. The resting mat 300 may comprise an interface 310. The interface 310 may be operable to accommodate and couple with the main body device 130.

The resting mat 300 may comprise a pair of mounts 320 configured to couple with an overhead bar from which toys and infant entertainment may hang. The resting may comprise a number of pressure sensitive points 330 located throughout the resting mat 300. The pressure sensitive points 330 may detect the movement of an infant on the mat. The pressure sensitive points may be operably coupled with the main body device 130. The main body device 130 may send to external device notifications concerning the infant's activity on the resting mat 300. For example, should an infant become dormant after a period of activity, or should an infant leave the resting mat 300, the main body device 130 may detect the lack of activity and send an alert to a smart device of a caretaker.

In some embodiments, the toys hanging from the overhead bar may comprise at least one gyroscope sensor. The at least one gyroscope sensor may detect movement of the hanging toys, such as movement caused by an infant hitting or playing with the toys.

In some embodiments, the gyroscope data and data obtained from the pressure sensitive points 330 may be compiled into an activity score by the main body device 130 or by a caretaker's smart device. Based on the activity score, a caretaker may receive a recommendation for more or less "tummy time" for the infant that day.

In some embodiments, the resting mat 300 may comprise a communication device 340, such as a Bluetooth or near field communication device. The communication device may be operably coupled with the main body device 130. The communication device 130 may communicate information gathered from the main body device to an external location. The external location may comprise the smart device of a caregiver. In some embodiments, the main body device 130 may communicate to the caregiver, via the communication device 340, information regarding the infant's activity. In further embodiments, the main body device 130 may communicate to the caregiver, via the communication device 340, suggestions regarding recommended activity for the infant or may provide recommended or suggested exercises for the caregiver to participate in with the infant present to encourage interaction with the infant and well-being for the caregiver.

Figure 7:
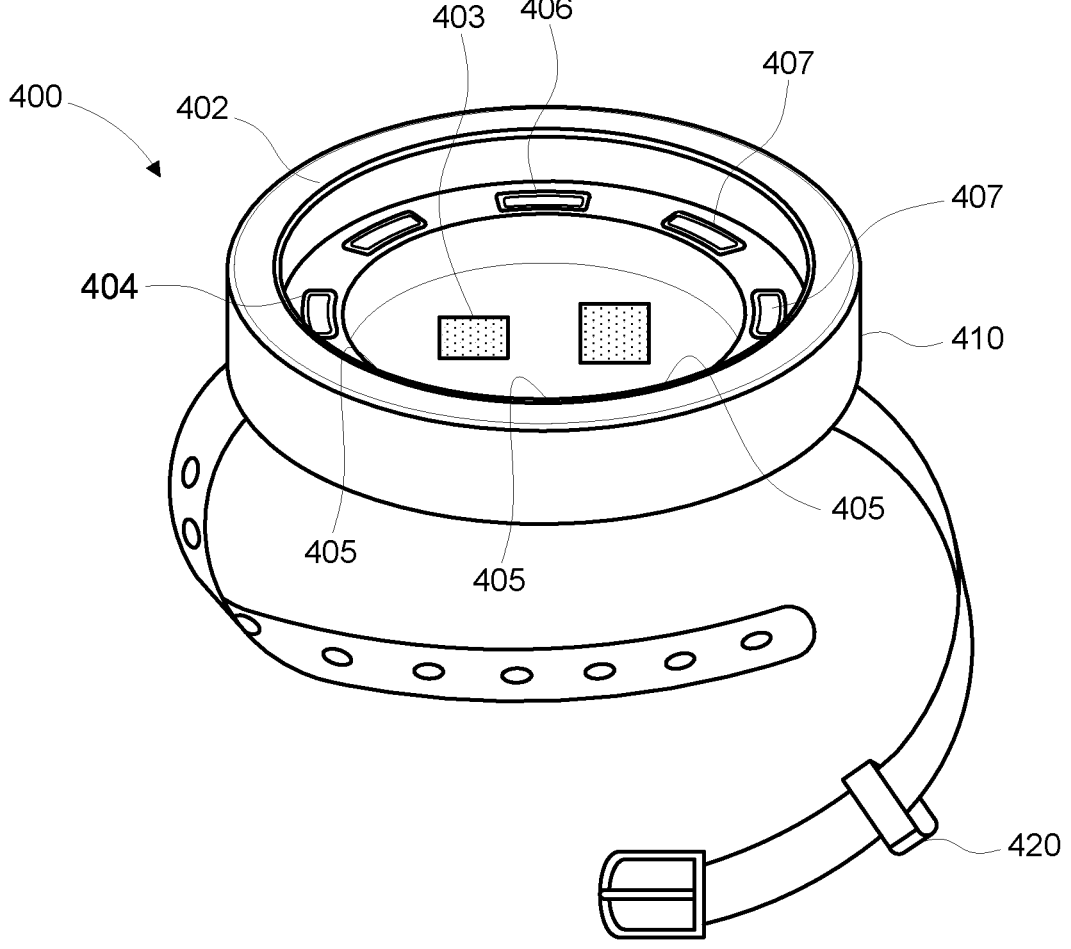
FIG. 7 is an illustration of a feature of the infant monitoring system.

Referring now to FIG. 7, in some embodiments, a harness 400 may be operable to couple with the main body device 130. The harness 400 may comprise a mount 402 operable to be coupled with the first member 131 of the main body device 130. The mount 402 may comprise a global positioning system (GPS) locator 403. The GPS locator 403 may locate coordinates of the harness 400 and communicate those coordinates to an external server or smart device via a long-range transceiver, as discussed below.

The mount 402 may comprise a number of contact pins. The contact pins may comprise a 3V connector pin 404, GPS communication pins 405, ground connector pin 406, and long range (LoRa) transceiver pins 407. The pins 404-407 may interface with the main body device 130. The first member 131 may be operable to communicate GPS position to an external server or smart device via the LoRa transceiver.

In some embodiments, the harness 400 may comprise a battery 410. The battery 410 may be positioned internally within the harness. The battery 410 may be operably coupled with the main body device 130 and provide additional power to the LCD screen 135 of the first member 131.

In some embodiments, the harness may comprise an adjustable collar 420, configured to fit about an infant's body, arm, leg, wrist, or ankle.

Figure 8:
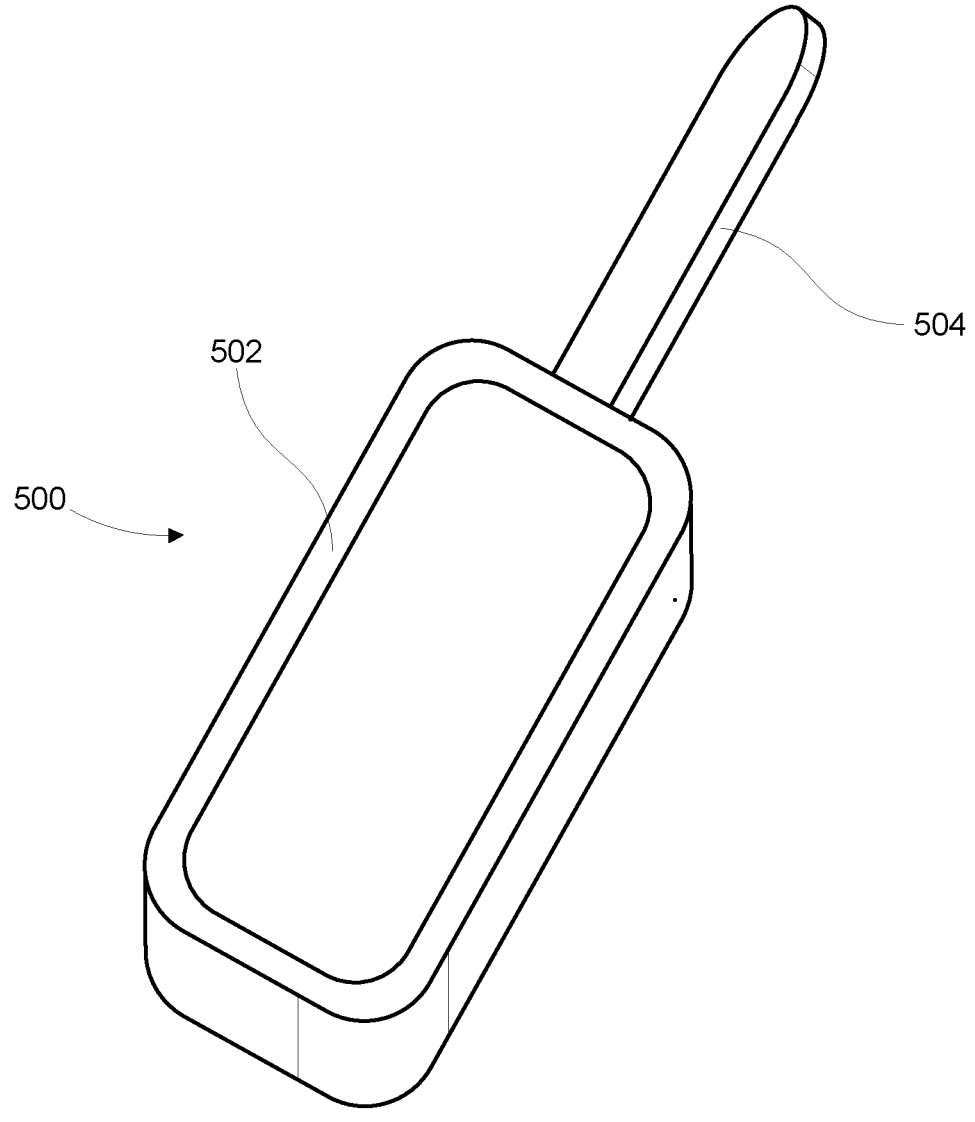
FIG. 8 is an illustration of a feature of the infant monitoring system.

Referring now to FIG. 8, in some embodiments, main body device 130 may be in communication with an external server or a smart device. In some embodiments, the smart device may comprise a companion device 500. The companion device 500 may serve as a monitor for the swaddle suit 100. The companion device 500 may be operably coupled with the swaddle suit 100 via near field communications, such as Bluetooth technology. The companion device 500 may be operably coupled with the swaddle suit via LoRa radio signal. Information transmitted via LoRa radio may be limited to position information, such as GPS coordinates. Such information may enable a caregiver to locate a lost or abducted child.

In some embodiments, the companion device 500 may comprise a display screen 510. The display may be configured to display information received from the main body device 130 of the main body device 130. Such information may include heart rate, blood-oxygen levels, GPS position, breathing patterns, body temperature, extremity temperatures, UV light and sunlight dosage, activity score, and recommendations for more activity, more or less sunlight, and sleep. The display may also display alarms in the event of an emergency.

In some embodiments, a swaddle suit may comprise other embodiments of the main body device. As shown in FIGS. 9-12, other embodiments of a main body device are also contemplated.

Figure 9:
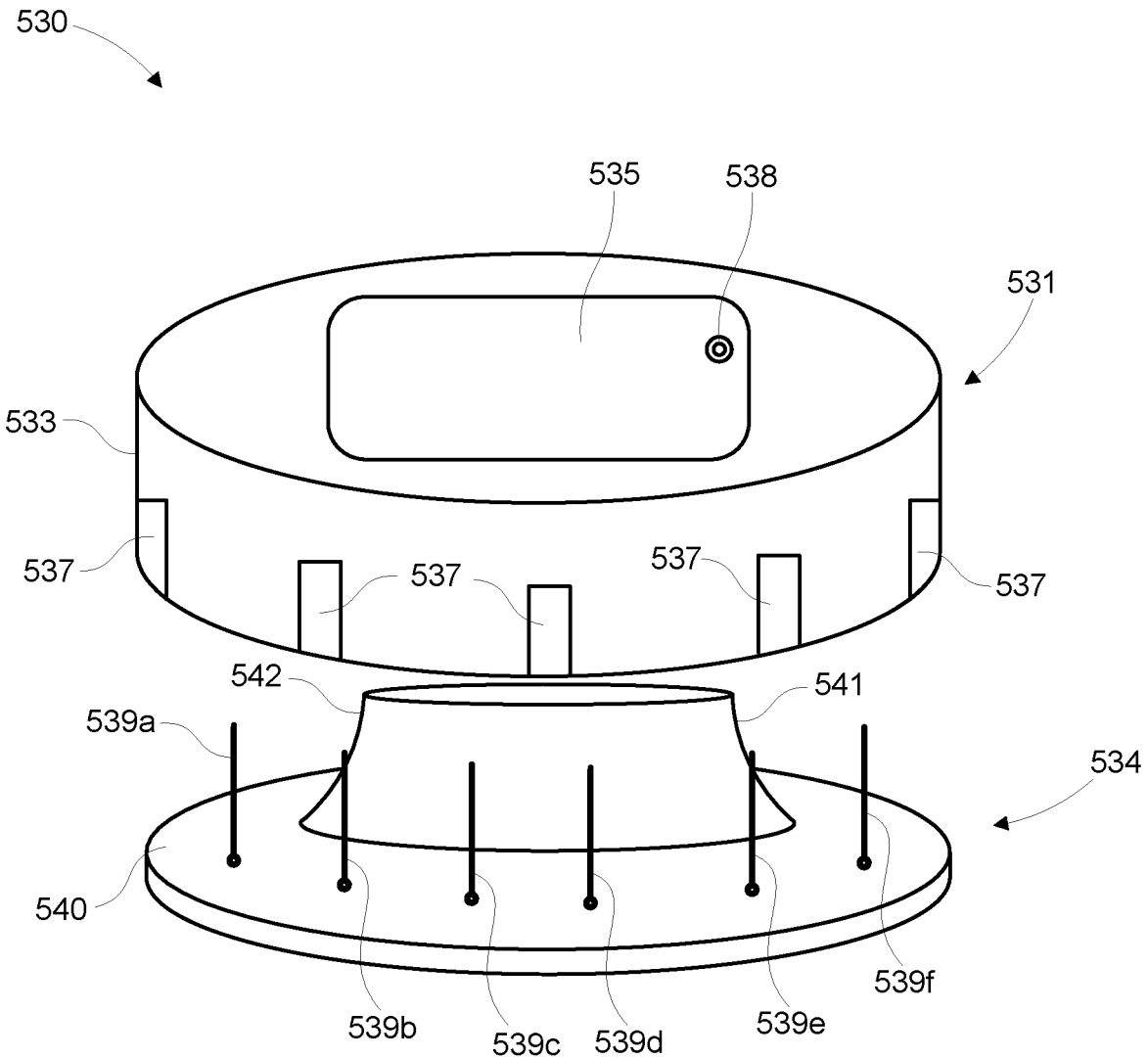
FIG. 9 is an illustration of a feature of the infant monitoring system.

Referring now to FIG. 9, some embodiments include a main body device 530 having a first member 531. The first member 531 may comprise a housing 533. The housing 533 may contain and/or support the components found within the first member 531.

The first member 531 may comprise a number of external contacts 537. Each external contact 537 may be operable to connect to a charging station and operably couple with contacts 537 the charging station. The main body device 530 may comprise a battery and may be charged via external contacts 537.

The first member 531 may comprise an LCD screen 535. The LCD screen 135 may be coupled with a processor and may display information gathered by various sensors as described below. The first member 531 may comprise a UV sensor 538.

The main body device 530 may comprise a second member 534. The second member 534 may comprise a body 540.

The body 540 may comprise various components that may receive and process data from the swaddle suit 500 and that may transmit data to an external server or to a smart device. The body 540 may comprise an electrocardiogram 570, as described below. The electrocardiogram 570 may be configured to monitor an infant's heart rate via electrical impulses produced by the body. The body 540 may comprise a pulse oximeter 580 as described below. The pulse oximeter 580 may monitor heart rate and blood-oxygen saturation.

The body 540 may comprise a temperature sensing system coupled with a series of temperature sensors, as described below. The body 540 may also comprise a core temperature sensor that may measure the core temperature of an infant. In some embodiments, the main body device may be in communication with a home heating and air conditioning system. Should the infant's temperature be out of a normal or comfortable range, the home heating and air conditioning system may be activated to warm or cool the environment as needed.

The body 540 may further comprise an electronic stethoscope 541. The electronic stethoscope may comprise a sensor within the body 540. The electronic stethoscope 541 may receive an acoustic signal representing an infant's heartbeat. The processor within the main body device 530 may use extrapolate heart rate and breathing aspirations using digital signal processing and artificial intelligence to monitor heart rate and perform an early diagnosis of respiratory and heart disease.

The body 540 may comprise a gyroscope 542. The gyroscope 542 may monitor aspirations by measuring the rise and fall of an infant's chest.

The second member 534 may comprise at least one internal contact 539. The at least one internal contact 539 may comprise multiple internal contact points 539*a*, 539*b*, 539*c*, 539*d*, 539*e*, and 539*f*. Each contact point 539*a*-539*f* may correspond to a different sensor within a swaddle suit.

Figure 10A:
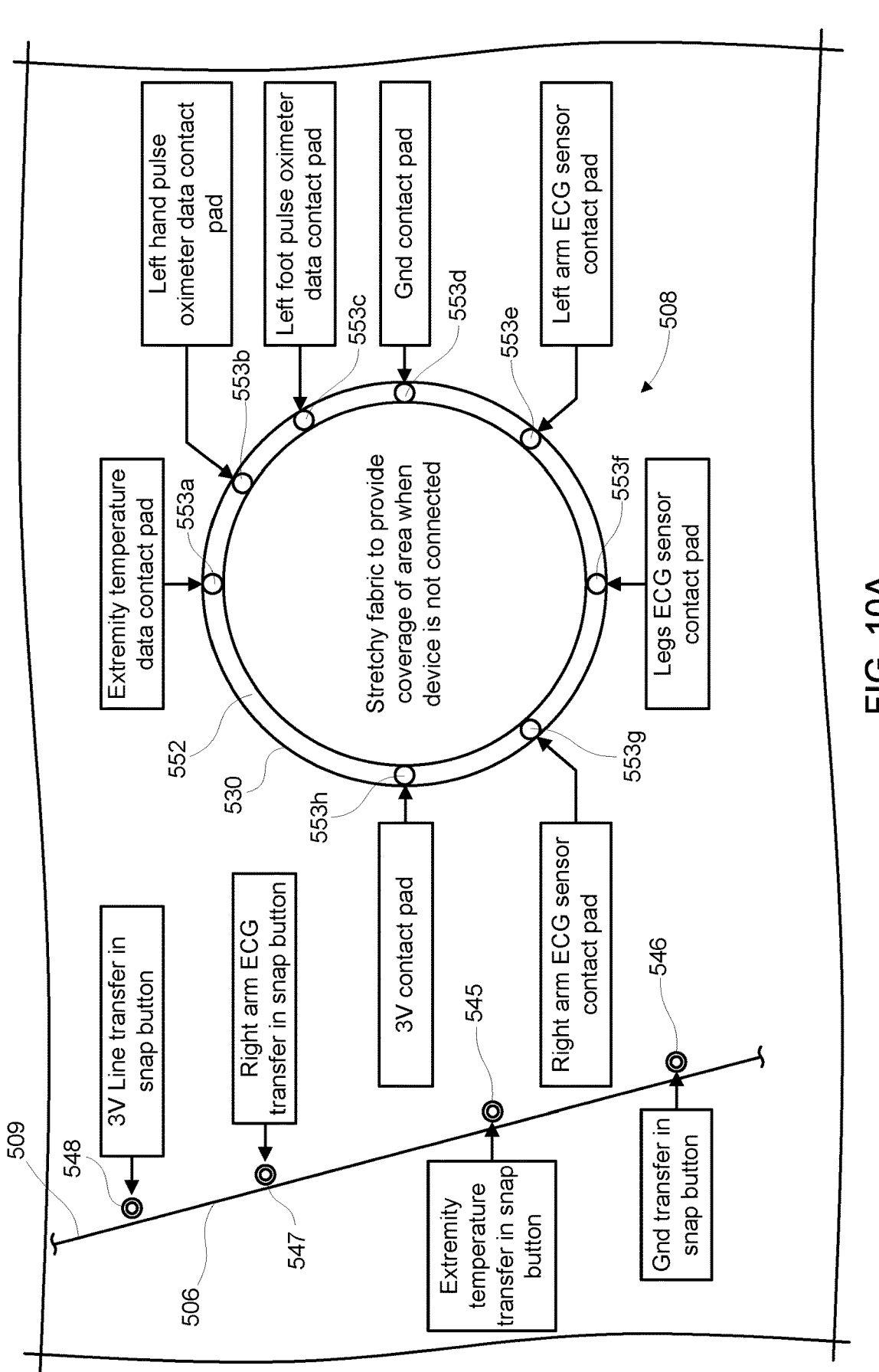
FIG. 10A is an illustration of a feature of the infant monitoring system.

FIG. 10A illustrates an opening 550 within a swaddle suit, similar to opening 150 described above. The opening 550 may comprise a contact ring 552. The contact ring 552 may comprise multiple contact pads 553. Each contact pad 553 may be detachably coupled with a sensor of a swaddle suit. For example, in some embodiments, the contact pad 553*a* may be operably connected with the extremity temperature sensor. The contact pad 553*b* may be operably connected with the pulse oximeter 582. The contact pad 553*c* may be operably connect with the pulse oximeter 584. The contact pad 553*d* may be operably coupled the ground. The contact pad 553*e* may be operably coupled with the electrocardiogram sensor 574. The contact pad 553*f* may be operably coupled with the electrocardiogram sensor 576. The contact pad 553*g* may be operably coupled with the electrocardiogram sensor 574. The contact pad 553*h* may be operably coupled with the 3V line.

The main body device 530 may be operable to couple with a swaddle suit at the contact pad ring 552. Each contact pin 539*a* through 539*h* may couple with respective contact pads 553*a* thorough 553*h*. When the contact pins 539 are engaged with the contact pads 553, the surface of the second member 534 may be in contact with the skin of an infant wearing a swaddle suit.

Figure 10B:
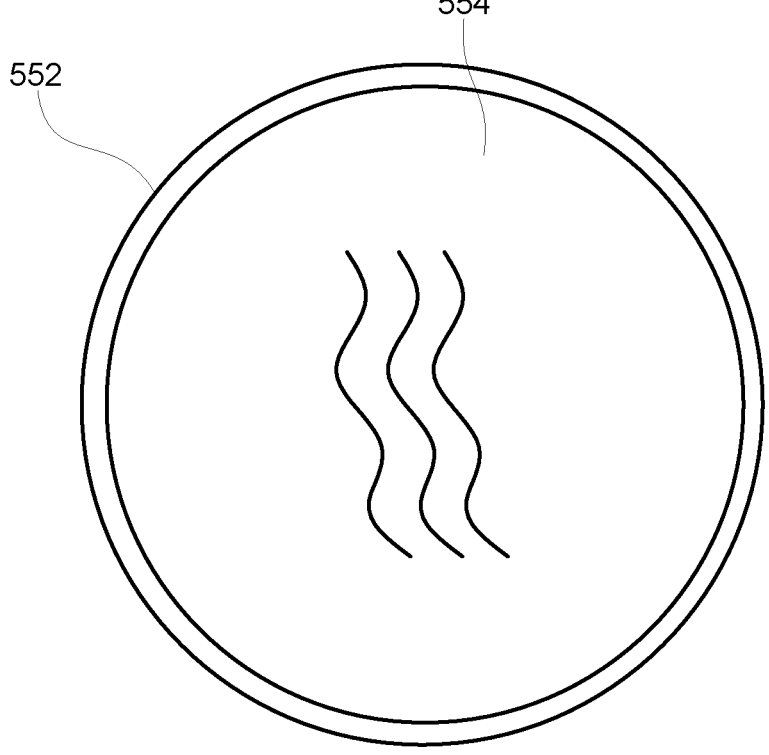
FIG. 10B is an illustration of a feature of the infant monitoring system.
Figure 11:
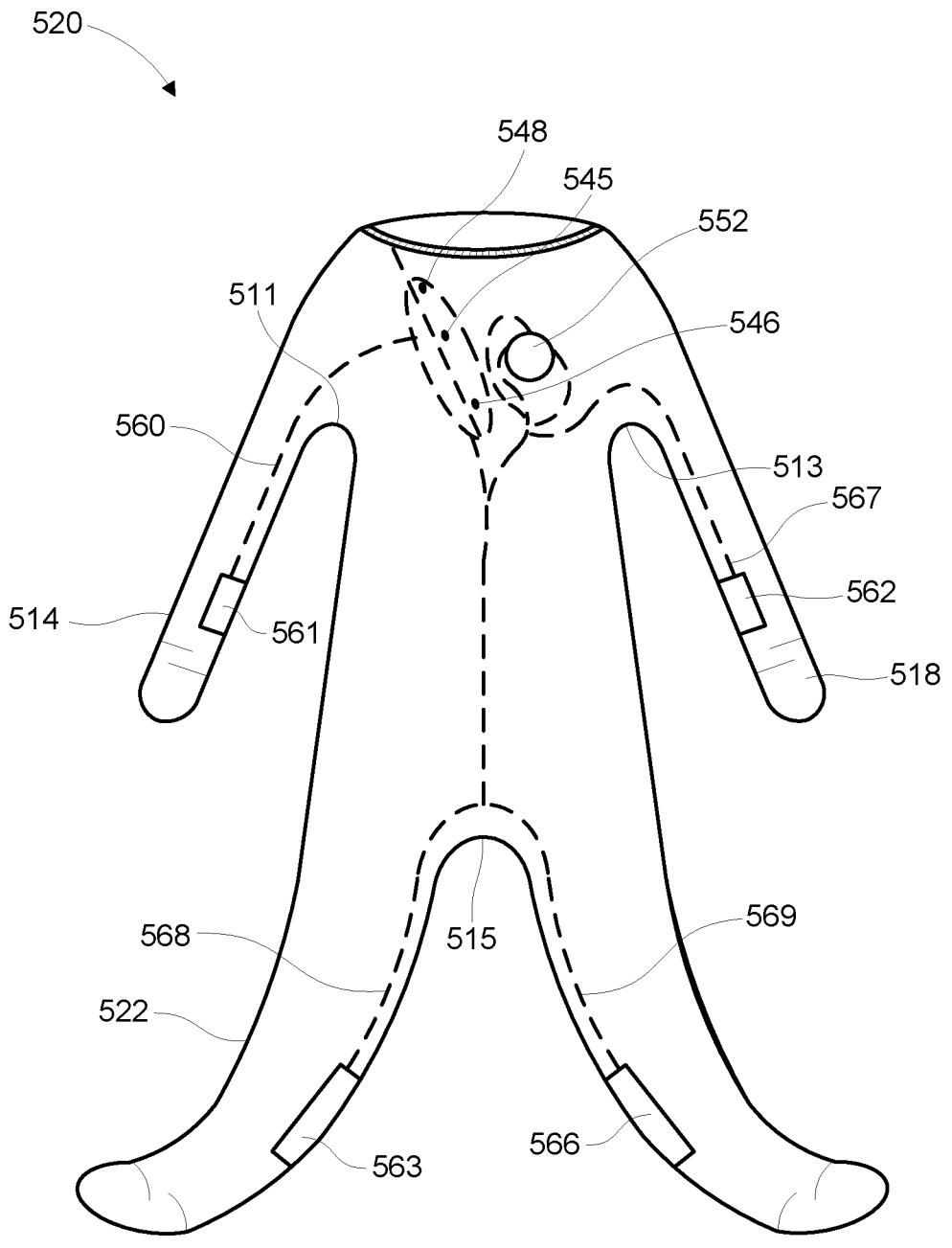
FIG. 11 is an illustration of a front view of the infant monitoring garment showing various internal components.

FIG. 10B illustrates the opening 550. In some embodiments, when the main device is not coupled with the contact pad ring 552, the opening 550 may be covered by a cover shield 554. The cover shield 554 may provide coverage of the opening 550. The cover shield 554 may comprise a fabric such as spandex, nylon, or other fabric with similar properties.

FIG. 4 illustrates a view of a swaddle suit 520 showing various components of the swaddle suit 520, including those components discussed relative to FIGS. 9-10B. In some embodiments, the swaddle suit 520 may comprise a temperature sensor 561 located in the right arm 514 near the wrist opening 516. The temperature sensor 561 may be operably coupled with the contact pad 552 via wire 560. The wire 560 may comprise a package of three wires. The three wires may comprise a three-volt (3V) wire, a data wire, and a ground wire. The wire may be coupled with the contact pad 552, and subsequently, the main body device 530, via at least one transfer point in a snap button. In some embodiments, the transfer point in a snap button may accommodate all three wires (i.e., the 3V wire, the data wire, and the ground wire) or there may be multiple snap buttons that accommodate the three wires, such as, for example, two snap buttons or three snap buttons.

In some embodiments, the, the 3V wire may be coupled with snap button transfer point 548. In some embodiments, the data wire may be coupled with the snap button transfer point. In some embodiments, the ground wire may be coupled with the snap button 546.

In some embodiments, the wire 560 may be placed in the swaddle suit 520 along the sewed seam for as far as possible, until approximately the armpit 511, at which point 3V wire, data wire, and ground wire split to travel to their respective snap button transfer points. Such a configuration may allow for wires to route around the front of the swaddle suit 520. Such a configuration will allow an infant to lay on the infant's back without the discomfort of wires between the infant and a sleeping or resting surface. Further, such a configuration also allows the swaddle suit 520 to open to allow an infant to be placed in the swaddle suit 520 or have the swaddle suit 520 removed from the infant.

In some embodiments, the swaddle suit 520 may comprise a second temperature sensor 562 located on the left arm 518 proximate to the wrist 520. The second temperature sensor 562 may be operably coupled with the contact pad 552 via wire 567. The wire 567 may comprise a package of three wires. The three wires may comprise a three-volt (3V) wire, a data wire, and a ground wire. The wire 567 may be coupled with the contact pad 552, and subsequently, the main body device 530 via at least one transfer point in a snap button, as detailed above with respect to the first temperature sensor 561.

In some embodiments, the 3V wire may be coupled with snap button transfer point 548. In some embodiments, the data wire may be coupled with the snap button transfer point 545. In some embodiments, the ground wire may be coupled with the snap button 546.

In some embodiments, the wire 567 may be placed in the swaddle suit 520 along the sewed seam for as far as possible, until approximately the armpit 513, at which point 3V wire, data wire, and ground wire split to travel to their respective snap button transfer points. Such a configuration may allow for wires to route around the front of the swaddle suit 520. Such a configuration will allow an infant to lay on the infant's back without the discomfort of wires between the infant and a sleeping or resting surface.

In some embodiments, the swaddle suit 520 may comprise a third temperature sensor 563 located on the right leg 522 proximate to the foot 524. The third temperature sensor 563 may be operably coupled with the contact pad 552 via wire 568. The wire 568 may comprise a package of three wires. The three wires may comprise a three-volt (3V) wire, a data wire, and a ground wire. The wire 568 may be coupled with the contact pad 552, and subsequently, the main body device 530 via at least one transfer point in a snap button.

In some embodiments, the, the 3V wire may be coupled with snap button transfer point 548. In some embodiments, the data wire may be coupled with the snap button transfer point 545. In some embodiments, the ground wire may be coupled with the snap button 546.

In some embodiments, the wire 568 may be placed in the swaddle suit 520 along the sewed seam for as far as possible, until approximately the groin 515. The wire 568 may continue as a package until reaching an area proximate the snap button transfer points, at which point 3V wire, data wire, and ground wire split to travel to their respective snap button transfer points.

In some embodiments, the swaddle suit may comprise a fourth temperature sensor 566 located on the left leg 526 proximate to the foot 528. The fourth temperature sensor 566 may be operably coupled with the contact pad 552 via wire 569. The wire 569 may comprise a package of three wires. The three wires may comprise a three-volt (3V) wire, a data wire, and a ground wire. The wire 569 may be coupled with the contact pad 552, and subsequently, the main body device 530 via at least one transfer point in a snap button.

In some embodiments, the, the 3V wire may be coupled with snap button transfer point 548. In some embodiments, the data wire may be coupled with the snap button transfer point 545. In some embodiments, the ground wire may be coupled with the snap button 546.

In some embodiments, the wire 569 may be placed in the swaddle suit 520 along the sewed seam for as far as possible, until approximately the groin 515. The wire 569 may continue as a package until reaching an area proximate the snap button transfer points, at which point 3V wire, data wire, and ground wire split to travel to their respective snap button transfer points.

Each of the temperature sensors described herein may be housed within a conductive fabric.

Figure 12:
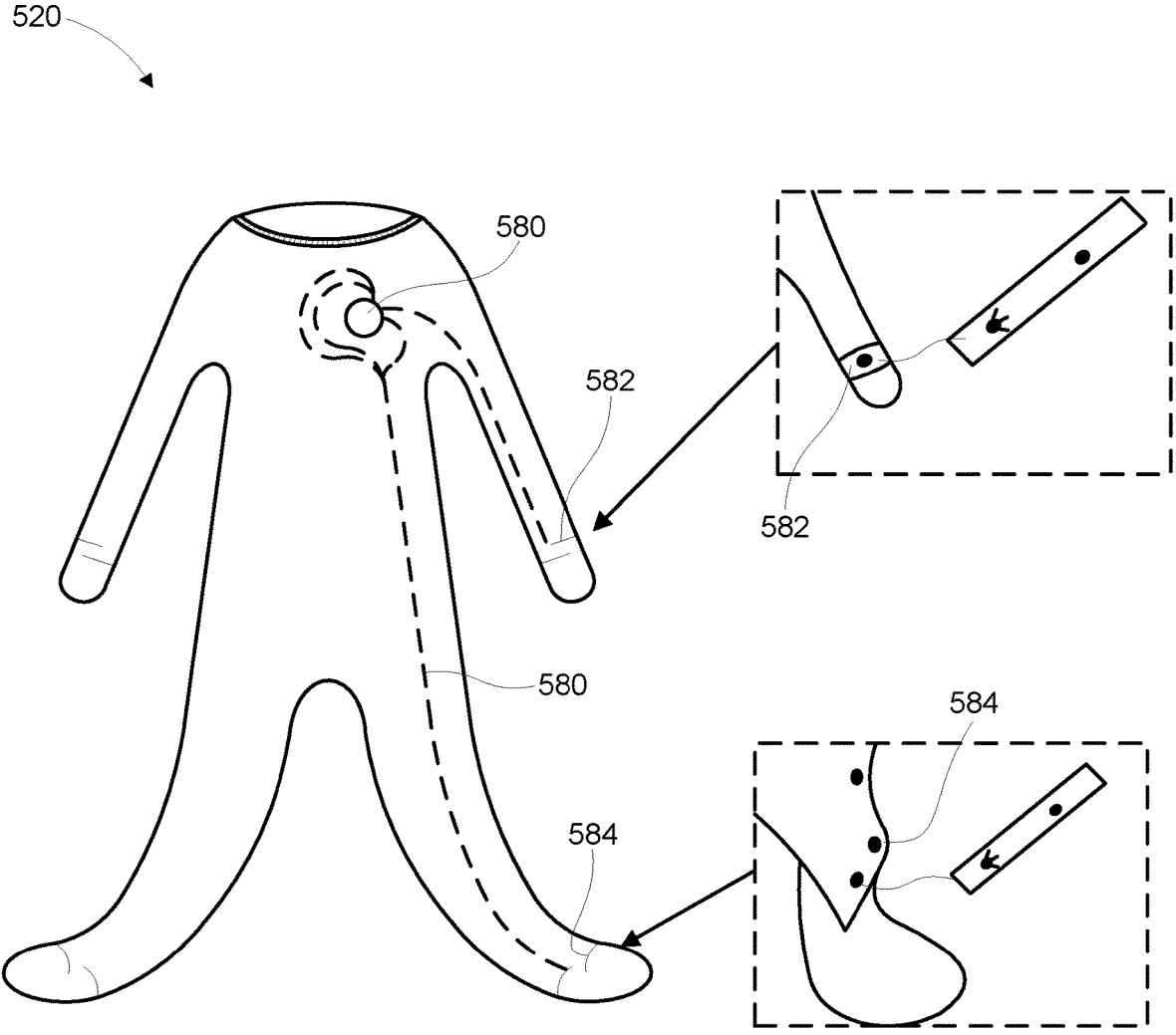
FIG. 12 is an illustration of a front view of the infant monitoring garment showing various internal components.

Referring now to FIG. 12, the main body device 530 may comprise a pulse oximeter 580. The pulse oximeter 580 may be comprised within the main body device 530 and is represented as being present is the same location as main body device 530 in FIG. 12. The pulse oximeter 580 may be operable to gather blood-oxygen saturation levels and measure a heart rate. The pulse oximeter 580 may be operably coupled with at least one sensor bracelet 582 via wire 581. The wire 581 may be routed along a seam of the front of swaddle suit 520. The at least one sensor bracelet 582 may take measurements reflecting blood oxygen levels and heart rate and communicate those measurements to the pulse oximeter 580. The at least one sensor 582 may be configured to be placed in the wrist area 520 of the swaddle suit 520 and may be configured to fit about an infant's wrist.

In some embodiments, the at least one sensor 582 may comprise a sensor 584. The sensor 584 may be operably coupled with the pulse oximeter 580 via wire 583. The wire 583 may be routed along a seam of the front of swaddle suit 520. The at least one sensor bracelet 584 may take measurements reflecting blood oxygen levels and heart rate and communicate those measurements to the pulse oximeter 580. The at least one sensor 584 may be configured to be placed in the foot area 526 of the swaddle suit 520 and may be configured to fit about an infant's ankle.

Figure 13:
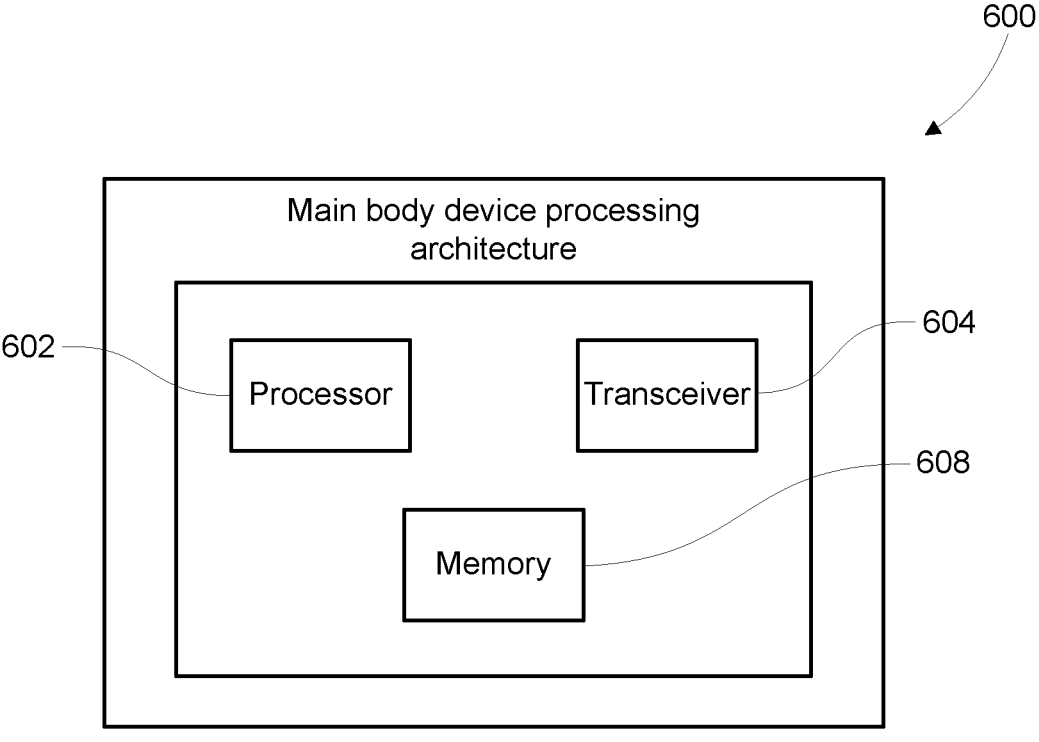
FIG. 13 is an illustration of various components of the infant monitoring garment.

In some embodiments, the main body device 130 and/or 530 may comprise various hardware architecture, as described above. FIG. 13 illustrates a block diagram of some embodiments of hardware architecture.

The block diagram architecture 600 may comprise a processor 602, a transceiver 604, a memory 606.

The processor 602 may process all information gather by the various sensors and measuring apparatuses of swaddle suit 100 or swaddle suit 520, in accordance with various embodiments of the present invention. Specifically, the processor 604 may be configured to execute program instructions stored in the memory 606 to perform the processes as required.

The transceiver or network module 604 may be configured to facilitate data exchange between the main body device and the other users.

The transceiver 214 may be configured to output messages from the main body device 130 or 530 for transmitting to an external location, as to a cloud architecture, to a network, or to an external device. Such network may include, but may not be limited to, any wired or wireless network, such as a radio network, LAN, or WAN, in accordance with various embodiments of the present invention. In some embodiments, the system described herein may be connected to a network and the information may be stored in a cloud architecture. In some embodiments, the swaddle suit 100 or the swaddle suit 530 may be used offline and may upload any newly entered, gathered, or received contents or data at a later time when a network connection is available.

The swaddle suit 100 and/or 520 may comprise a computational system that can be used to perform any of the embodiments of the invention. For example, computational system can be used to execute processes. As another example, the computational system can be used perform any calculation, identification and/or determination described here. The computational system includes hardware elements that can be electrically coupled via a bus (or may otherwise be in communication, as appropriate). The hardware elements can include one or more processors including without limitation one or more general-purpose processors and/or one or more special-purpose processors (such as digital signal processing chips, graphics acceleration chips, and/or the like); one or more input devices, which can include without limitation a mouse, a keyboard and/or the like; and one or more output devices, which can include without limitation a display device, a printer and/or the like.

The computational system may further include (and/or be in communication with) one or more storage devices, which can include, without limitation, local and/or network accessible storage and/or can include, without limitation, a disk drive, a drive array, an optical storage device, a solid-state storage device, such as a random access memory ("RAM") and/or a read-only memory ("ROM"), which can be programmable, flash-updateable and/or the like. The computational system might also include a communications subsystem, which can include without limitation a modem, a network card (wireless or wired), an infrared communication device, a wireless communication device and/or chipset (such as a Bluetooth device, an 802.6 device, a Wi-Fi device, a WiMax device, cellular communication facilities, etc.), and/or the like. The communications subsystem may permit data to be exchanged with a network (such as the network described below, to name one example), and/or any other devices described in this document. In many embodiments, the computational system will further include a working memory, which can include a RAM or ROM device, as described above.

The computational system also can include software elements, shown as being currently located within the working memory, including an operating system and/or other code, such as one or more application programs, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) described above.

In some cases, the storage medium might be incorporated within the computational system or in communication with the computational system. In other embodiments, the storage medium might be separate from a computational system (e.g., a removable medium, such as a compact disc, etc.), and/or provided in an installation package, such that the storage medium can be used to program a general-purpose computer with the instructions/code stored thereon. These instructions might take the form of executable code, which is executable by the computational system and/or might take the form of source and/or installable code, which, upon compilation and/or installation on the computational system (e.g., using any of a variety of generally available compilers, installation programs, compression/decompression utilities, etc.) then takes the form of executable code.

Unless otherwise specified, the term "substantially" means within 5% or 10% of the value referred to or within manufacturing tolerances. Unless otherwise specified, the term "about" means within 5% or 10% of the value referred to or within manufacturing tolerances.

The conjunction "or" is inclusive.

The terms "first", "second", "third", etc. are used to distinguish respective elements and are not used to denote a particular order of those elements unless otherwise specified or order is explicitly described or required.

Numerous specific details are set forth to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained in software to be used in programming or configuring a computing device.

Embodiments of the methods disclosed may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

That which is claimed:

1. An infant monitoring device, comprising:
   a suit for an infant;
   at least one flexible printed circuit board (PCB) coupled with the suit;
   a main body receptacle coupled with the suit and operably coupled with the at least one flexible PCB, wherein the main body receptacle comprises at least one electrical contact operably coupled with the at least one flexible PCB and at least one temperature sensor operably coupled with the flexible PCB and operable to measure body temperature; and
   a main body device detachably coupled with the main body receptacle, the main body device comprising at least one contact point operably coupled with the at least one electrical contact of the main body receptacle, and a battery operable to provide power to the main body device and the main body receptacle.

2. The infant monitoring device of claim 1, wherein the main body receptacle further comprises at least one electrocardiogram sensor operably coupled with the at least one flexible PCB.

3. The infant monitoring device of claim 1, wherein the main body receptacle further comprises at least one pulse oximeter sensor operably coupled with the at least one flexible PCB.

4. The infant monitoring device of claim 1, wherein the main body receptacle further comprises at least one electronic stethoscope operably coupled with the at least one flexible PCB.

5. The infant monitoring device of claim 1, wherein the main body device further comprises at least one external charging connection, an LCD screen, and a UV sensor.

6. The infant monitoring device of claim 1, further comprising a plurality of sensors and wherein:

the at least one electrical contact comprises a plurality of electrical contacts; and the at least one flexible PCB comprises a plurality of flexible PCBs, wherein the plurality of electrical contacts is operably coupled with the plurality of flexible PCBs; and, wherein each of the plurality of sensors is operably coupled with each of the plurality of flexible PCBS.

7. The infant monitoring device of claim 6, wherein each of the plurality of sensors is operably connected to each of the plurality of flexible PCBs via wired connections.

8. The infant monitoring device of claim 7, wherein the plurality of sensors comprises at least one of at least one extremity temperature sensor, at least one electrocardiogram sensor, and at least one extremity pulse oximeter sensor.

9. The infant monitoring device of claim 7, wherein wires of the wired connections are routed along seams of the suit.

10. The infant monitoring device of claim 7, wherein the suit comprises a plurality of snap buttons, wherein at least one of the plurality of snap buttons is electrically conductive.

11. The infant monitoring device of claim 10, wherein the at least one of the plurality of electrically conductive snap buttons is a transfer switch.

12. The infant monitoring device of claim 10, wherein the at least one of the plurality of electrically conductive snap buttons comprises a 3-volt line transfer.

13. The infant monitoring device of claim 10, wherein the at least one of the plurality of electrically conductive snap buttons comprises a transfer switch operably coupled to the at least one electrocardiogram sensor.

14. The infant monitoring device of claim 12, wherein the suit comprises a conductive fabric operably coupled to a connection device, wherein the conductive fabric is operable to provide at least one electrocardiogram sensor with electrical impulses from a wearer's body.

15. The infant monitoring device of claim 1, further comprising a video-capture device external to the suit, the video-capture device comprising a power charging station operable to couple with the main body device at at least one external charging connection.

16. An infant monitoring device, comprising:

a suit for an infant;

at least one flexible printed circuit board (PCB) coupled with the suit;

a main body receptacle coupled with the suit and operably coupled with the at least one flexible PCB, wherein the main body receptacle comprises:

at least one electrical contact operably coupled with the at least one flexible PCB and at least one temperature sensor operably coupled with the flexible PCB and operable to measure body temperature;

a gyroscope operably coupled to the at least one electrical contact;

at least one electrocardiogram sensor coupled to the main body receptacle and operably coupled to the at least one electrical contact;

at least one pulse oximeter sensor coupled to the main body receptacle and operably coupled to the at least one electrical contact; and at least one electronic stethoscope coupled to the main body receptacle and operably coupled to the at least one electrical contact; and a main body device detachably coupled with the main body receptacle, the main body device comprising:

at least one contact point operably coupled with the at least one electrical contact of the main body receptacle;

a battery charging port;

a rechargeable battery operable to provide power to the main body device and the main body receptacle;

a processor operably coupled with the at least one electrical contact;

a memory in communication with the processor;

a transceiver in communication with the processor and the memory, the transceiver being operable to transmit information to an external location and receive information from an external location;

a screen operably coupled with the processor and the memory, the screen being operable to display information related to measurements taken by the infant monitoring device; and an ultraviolet light sensor coupled with the screen.

17. The infant monitoring device of claim 16, further comprising at least one extremity temperature sensor operably coupled with the at least one electrical contact.

18. The infant monitoring device of claim 17, further comprising at least one extremity echocardiogram sensor operably coupled with the at least one electrical contact.

* * * * *